United States Patent [19]

van Andel

[11] Patent Number: Plant 6,035

[45] Date of Patent: Oct. 6, 1987

[54] ALSTROEMERIA NAMED STALRIN

[75] Inventor: Jacob van Andel, Aalsmeer, Netherlands

[73] Assignee: Van Staaveren B.V., Aalsmeer, Netherlands

[21] Appl. No.: 805,209

[22] Filed: Dec. 5, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler; John B. Lungmus

[57] ABSTRACT

A new and distinctive variety of Alstroemeria particularly distinguished by its continuous year around and profuse production of very large flowers of a distinctive generally orange red to fire red coloration borne singly on relatively long stems carried on tall canes, this plant having a strong and vigorous growth habit with abundant foliage; and the flowers having a relatively long lasting quality both on the plant and as cut flowers.

1 Drawing Figure

BACKGROUND OF THE NEW PLANT

This new Alstroemeria originated as a seedling resulting from my crossing of my breeding stock variety Or. 8 with my stock variety 9266-4 at Aalsmeer, The Netherlands, in 1981 with the object of developing a new type of plant and a new alstroemeria color. This particular seedling was selected by me for propagation because of its vigorous growth and its profuse production of very large flowers of a very different and distinctive color. Propagation of this new plant by root division has been carried on under my direction at Aalsmeer and successive generations of this new plant have demonstrated that the novel characteristics of the original hybrid parent are retained from generation to generation and appear to be firmly fixed.

DESCRIPTION OF THE DRAWING

My new alstroemeria cultivar is illustrated by the accompanying photographic drawings which shows the distinguishing color characteristics and flower form of the blossoms of this new plant, the color rendition being as nearly true as it is reasonably possible to obtain by conventional photographic procedures.

DESCRIPTION OF THE NEW PLANT

The following is a detailed description of my new alstroemeria cultivar with color designations according to The R.H.S. Colour Chart of The Royal Horticultural Society of London, England.

THE PLANT

Origin: Seedling.
Parentage:
- *Seed parent.*—Stock Plant Or. 8 (unpatented).
- *Pollen parent.*—Stock Plant 9266-4 (unpatented). Both plants being identified by my record of the plants comprising my breeding stock.

Classification:
- *Botanic.*—Alstroemeria Hybrid.
- *Commercial.*—Alstroemeria.

Form: Bush.
Height: About 175 cm.
Main stem or cane length: About 175 cm.
Growth: Vigorous, strong and upright.

Foliage:
- *Quantity.*—Abundant.
- *Number of leaves.*—Various, depending on season.
- *Size of leaf.*—Various, depending on season.
- *Shape of leaf.*—Elliptic.
- *Texture.*—Leathery.
- *Color.*—Upper side — Middle green. Under side — Middle green.

Rhizomes:
- *Color.*—White.
- *Size.*—Depends on season.

THE BUD

Form: Pear shaped.
Diameter: About 20 to 25 mm.
Length: About 50 mm.
Opening rate: Normal.
Calyx: This bud has no calyx and the six petals of the flower are a perianth.
Peduncle:
- *Length.*—About 20 mm.
- *Color.*—Middle green.
- *Character.*—The peduncle is sturdy and extends upwardly at an angle of about 30° from the main stem.

THE FLOWER

Blooming habit: Continuous and abundant the year around.
Flower size: Very large.
- *Diameter.*—About 55 to 60 mm.
- *Depth.*—About 55 to 60 mm.

Borne: Singly.
Shape: When bloom matures, funnel-like with the petal ends curving outwardly and having an obcordate apex.
Texture: Leathery.
Appearance: Satiny.
Color:
- *Lower petals.*—Top side — 33A/B. Reverse side — 34A/B.
- *Upper petals.*—17A with 21A+33A/B.
- *Reverse side.*—17A+34A/B.

Peduncle:
- *Length.*—About 20 mm.
- *Color.*—Middle green.

Persistence: The flowers hang on and dry.
Lasting quality:
*On plant.*—About 10 to 15 days.
*As cut flower.*—About 7 to 9 days.

REPRODUCTIVE ORGANS

Stamens:
*Number.*—Six, there being one opposite each petal.
Anthers:
*Color.*—Olive green.
Filaments:
*Color.*—Orange red.
Pistils:
*Number.*—One.
*Color.*—Orange red.
Stigma:
*Color.*—Orange red.

FRUIT

Fertility: The fruit is fertile.
Shape: Capsular.
Color at maturity: Light brown.

This Alstroemeria variety is new in almost all respects and is particularly distinguished by its very large flowers of a generally orange-red coloration, and its continuous year around flower production.

I claim:

1. A new and distinctive Alstroemeria variety, substantially as herein shown and described, characterized by its abundant production of very large flowers of a generally orange-red coloration, its abundant foliage, and its tall flowering stems.

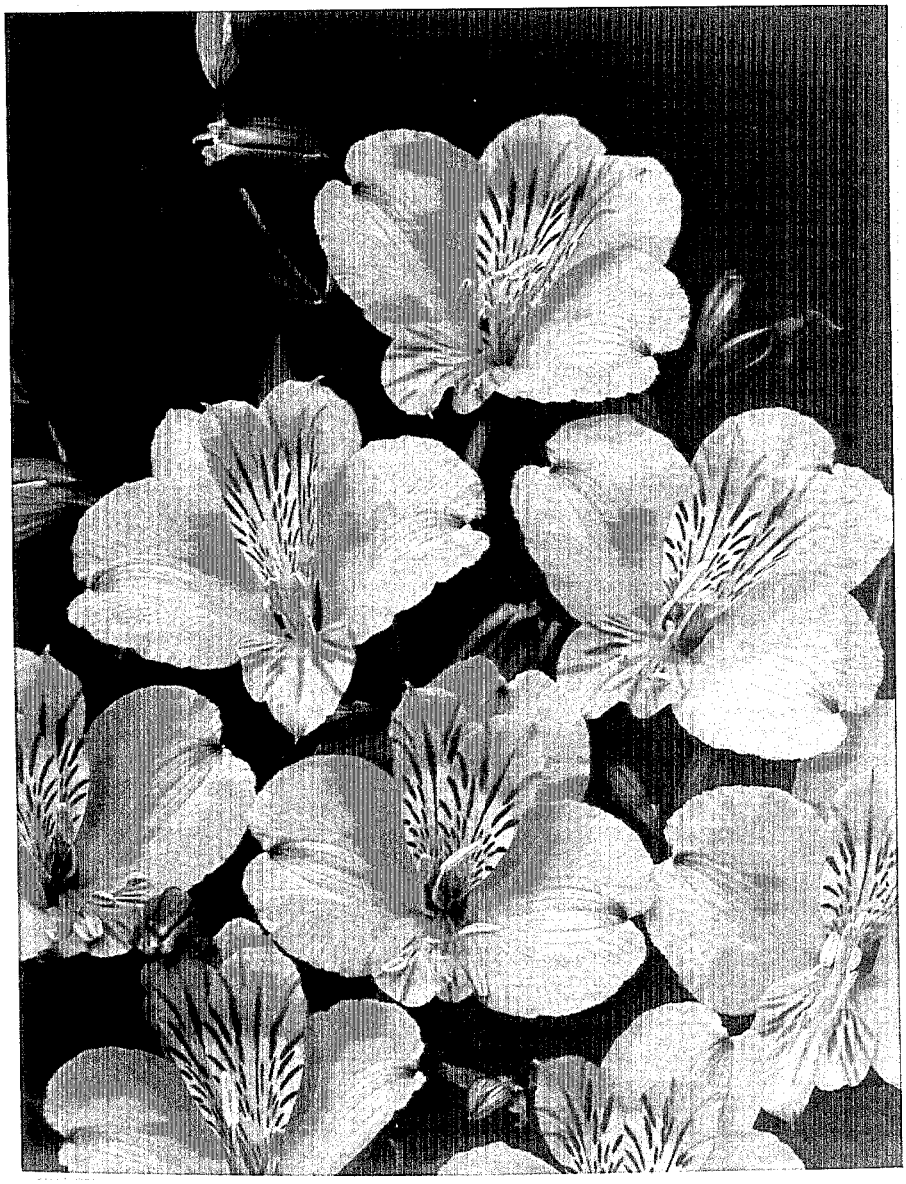

* * * * *